United States Patent
Alotaibi et al.

(10) Patent No.: US 12,336,892 B1
(45) Date of Patent: Jun. 24, 2025

(54) DISPOSABLE GAUZE COUNTER

(71) Applicant: KING SAUD UNIVERSITY, Riyadh (SA)

(72) Inventors: Mohammed Nawar Alotaibi, Riyadh (SA); Nuha Abdlrahman Alsaleh, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/069,159

(22) Filed: Mar. 3, 2025

(51) Int. Cl.
*A61B 17/06* (2006.01)
*A61F 13/36* (2006.01)
*A61F 13/84* (2006.01)

(52) U.S. Cl.
CPC .............. *A61F 13/36* (2013.01); *A61F 13/84* (2013.01); *A61F 2013/8497* (2013.01)

(58) Field of Classification Search
CPC . A61B 50/37; A61B 2090/0804; A45C 13/02; A61F 13/36; A61F 13/84; A61F 2013/8497; A61F 15/001; A61F 15/007; B65D 73/0014; B65D 73/005
USPC ................ 206/1.5, 361, 362, 370, 438, 440, 206/477–480, 482, 526; 211/16, 45, 59.1, 211/89.01; 248/201, 222.11; 604/4.01, 604/8–10, 317–319, 327, 355, 374
See application file for complete search history.

(56) References Cited

U.S. PATENT DOCUMENTS

| | | |
|---|---|---|
| 4,234,086 A | 11/1980 | Dorton |
| 4,342,390 A | 8/1982 | Mitchell et al. |
| 4,422,548 A | 12/1983 | Cheesman et al. |
| 4,429,789 A * | 2/1984 | Puckett, Jr. ............ A61B 50/37 220/555 |
| 4,634,005 A * | 1/1987 | Kulzer ............... B65D 73/0064 206/349 |
| 4,887,715 A | 12/1989 | Sphan et al. |
| 5,348,152 A * | 9/1994 | Kiyoshi ................. A45D 27/24 206/480 |
| 5,535,881 A * | 7/1996 | Krivec ................... B25H 3/003 206/483 |
| 6,076,669 A * | 6/2000 | Ling .................. B65D 73/0064 206/349 |
| 7,249,682 B2 * | 7/2007 | Lacatus ................. B65D 85/48 211/41.14 |
| 8,069,998 B2 * | 12/2011 | Thomas ................ A61B 50/34 206/370 |
| 8,371,448 B1 | 2/2013 | Reax |
| 9,814,631 B2 | 11/2017 | Choudhury et al. |
| 2008/0030303 A1 | 2/2008 | Kobren et al. |
| 2017/0095048 A1 | 4/2017 | Kohn et al. |

* cited by examiner

*Primary Examiner* — Luan K Bui
(74) *Attorney, Agent, or Firm* — Nath, Goldberg & Meyer; Joshua B. Goldberg

(57) ABSTRACT

A disposable gauze counter is provided having opposing first and second ends and opposing top and bottom sides, with a plurality of resealable airtight clips disposed between the first end and the second end and generally extending from the top side of the disposable gauze counter towards the bottom side of the disposable gauze counter. The plurality of resealable airtight clips each comprise an opening having opposed first and second sides, the first side and the second side each having at least one engaging member disposed thereon, wherein when the first side and the second side are pressed together the engaging members form an interlocking seal.

9 Claims, 5 Drawing Sheets

DISPOSABLE GAUZE COUNTER

FIELD AND BACKGROUND OF THE INVENTION

The disclosure of the present patent application relates to surgical tools and particularly to a disposable gauze counter for securing, counting, and displaying surgical gauze or sponges used during a surgical procedure.

DESCRIPTION OF THE PRIOR ART

During surgical procedures, surgical gauzes, surgical sponges, and the like are used to absorb bodily fluids. These gauzes, sponges, and the like must all be removed prior to the conclusion of the procedure. Accordingly, devices for the storage and display of used surgical gauzes, sponges, and the like have been developed. Depending upon the procedure, the gauzes used during these procedures may fall into different categories, which may relate to the size of the gauze or other identifying characteristics. Surgical teams may find it easier to track gauzes based upon the number and type used.

As exemplified by U.S. 2008/0030303 A1, these devices generally include containers having a plurality of pockets sealed on three sides and open on the top. The pockets may be numbered, and may be made of a see-through material to allow visual confirmation of the number of used surgical gauzes, sponges, and the like that have been used and removed during the procedure. Notably, these devices do not allow a surgeon to separately track the number of gauzes of various types.

Thus, a disposable gauze counter solving the aforementioned problems is desired.

SUMMARY OF THE INVENTION

The disposable gauze counter includes a plurality of resealable airtight clips. Each disposable gauze counter has opposing first and second ends and opposing top and bottom sides, with the plurality of resealable airtight clips disposed between the first end and the second end of the disposable gauze counter and generally extending from the top side of the disposable gauze counter towards the bottom side of the disposable gauze counter. The plurality of resealable airtight clips each comprise an opening having opposed first and second sides, the first side and the second side each having at least one engaging member disposed thereon, wherein when the first side and the second side of each opening are pressed together the engaging members form an interlocking seal.

In an alternative embodiment, the disposable gauze counter includes a plurality of resealable airtight clips. According to this embodiment, each disposable gauze counter has opposing first and second ends and opposing top and bottom sides, with the plurality of resealable airtight clips disposed between the first end and the second end of the disposable gauze counter and generally extending from the top side of the disposable gauze counter towards the bottom side of the disposable gauze counter. The plurality of resealable airtight clips each comprise an opening having opposed first and second sides, the first side and the second side each having a pair of engaging members disposed thereon, wherein when the first side and the second side of each opening are pressed together each of the pair of the engaging members form interlocking seals.

In another alternative embodiment, a plurality of disposable gauze counters are provided, and each disposable gauze counter includes a plurality of resealable airtight clips as described herein. Each of the plurality of disposable gauze counters has a label extending from the first end to the second end along the bottom side and below the plurality of resealable airtight clips, wherein the label identifies the particular disposable gauze counter as being specifically used to retain surgical gauze, surgical towels, radio-opaque gauze, or the like.

In a further embodiment, a disposable gauze system is provided comprising a plurality of disposable gauze counters as described herein.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1A:
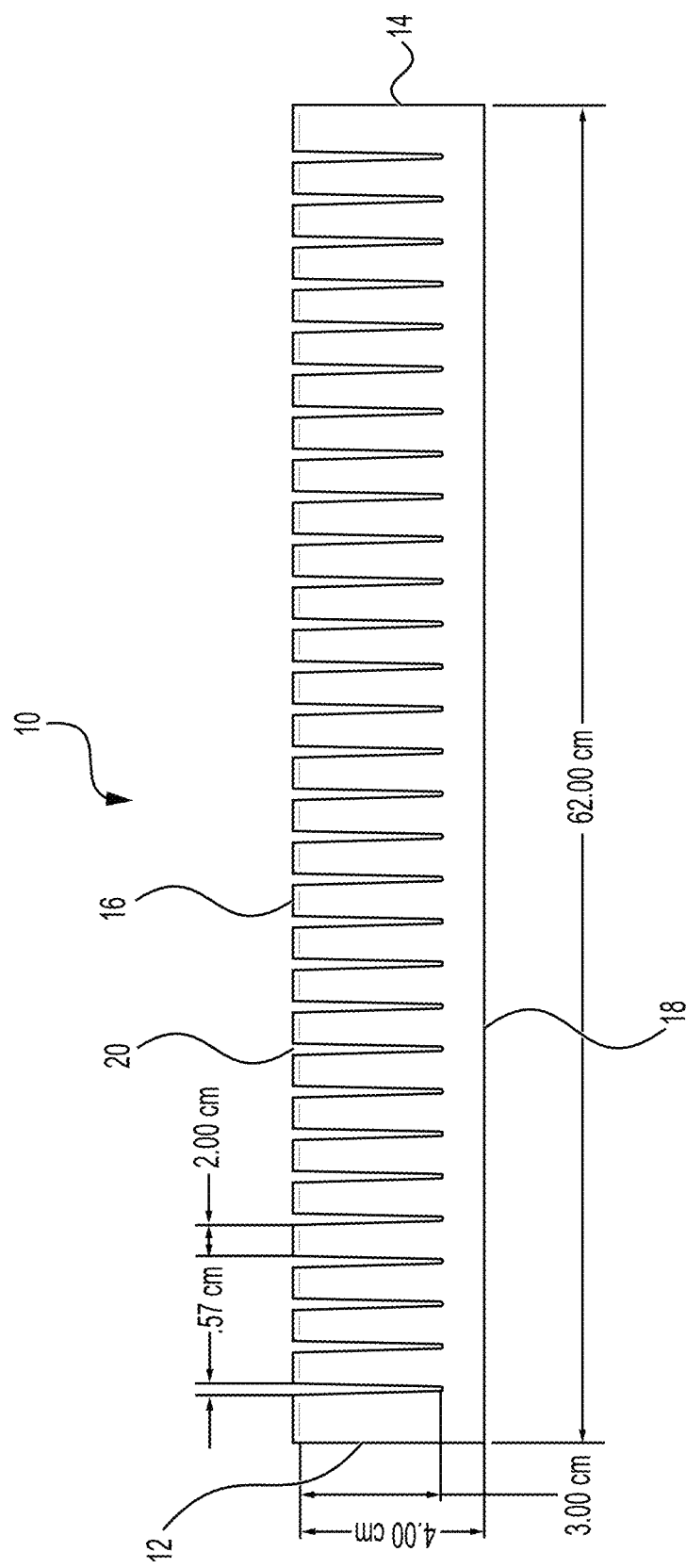
FIG. 1A is a side view of a disposable gauze counter according to the present subject matter.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where devices are described as having, including, or comprising specific components, or where processes are described as having, including, or comprising specific process steps, it is contemplated that devices of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a device or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Figure 1B:
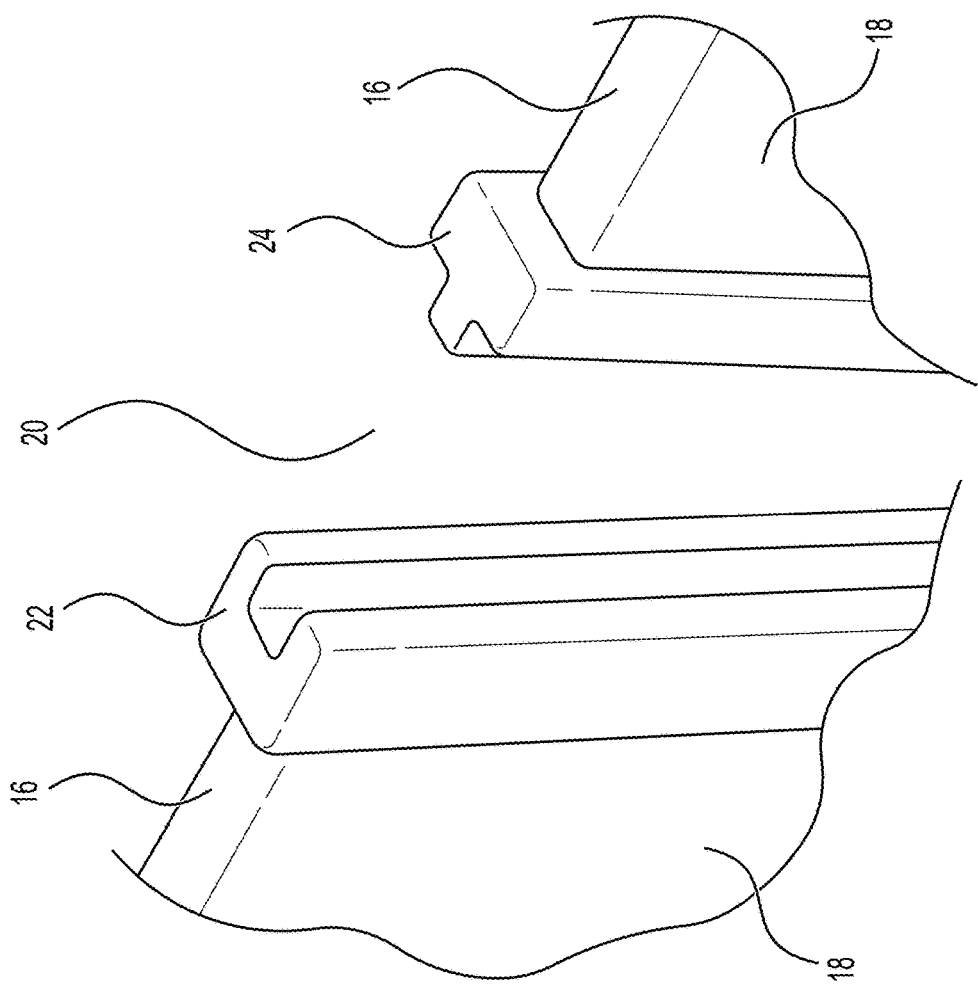
FIG. 1B is a perspective view of a disposable gauze counter illustrating one of the plurality of resealable airtight clips.

As illustrated in FIGS. 1A and 1B, the disposable gauze counter 10 includes a plurality of resealable airtight clips 20. Each disposable gauze counter 10 has opposing first 12 and second ends 14, and opposing top 16 and bottom sides 18, with each of the plurality of resealable airtight clips 20 disposed between the first end 12 and the second end 14 and generally extending from the top side 16 of the disposable gauze counter 10 towards the bottom side 18 of the disposable gauze counter 10. Each of the plurality of resealable airtight clips 20 can, but do not necessarily, extend all the way to the bottom side 18 of the disposable gauze counter 10. That is, each of the plurality of resealable airtight clips 20 can extend from the top side 16 of the disposable gauze counter 10 along part of the distance between the top side 16 and the bottom side 18 of the disposable gauze counter 10. In an embodiment, each of the resealable airtight clips 20 have a same length. In another embodiment, each of the resealable airtight clips 20 have a different length.

The plurality of resealable airtight clips 20 each comprise an opening having opposed first and second sides, the first side and the second side of each opening each having at least one engaging member 22, 24 disposed thereon, wherein when the at least one first side engaging member 22 and the at least one second side engaging member 24 of a same opening are pressed together the engaging members 22, 24 form an interlocking seal.

Figure 2A:
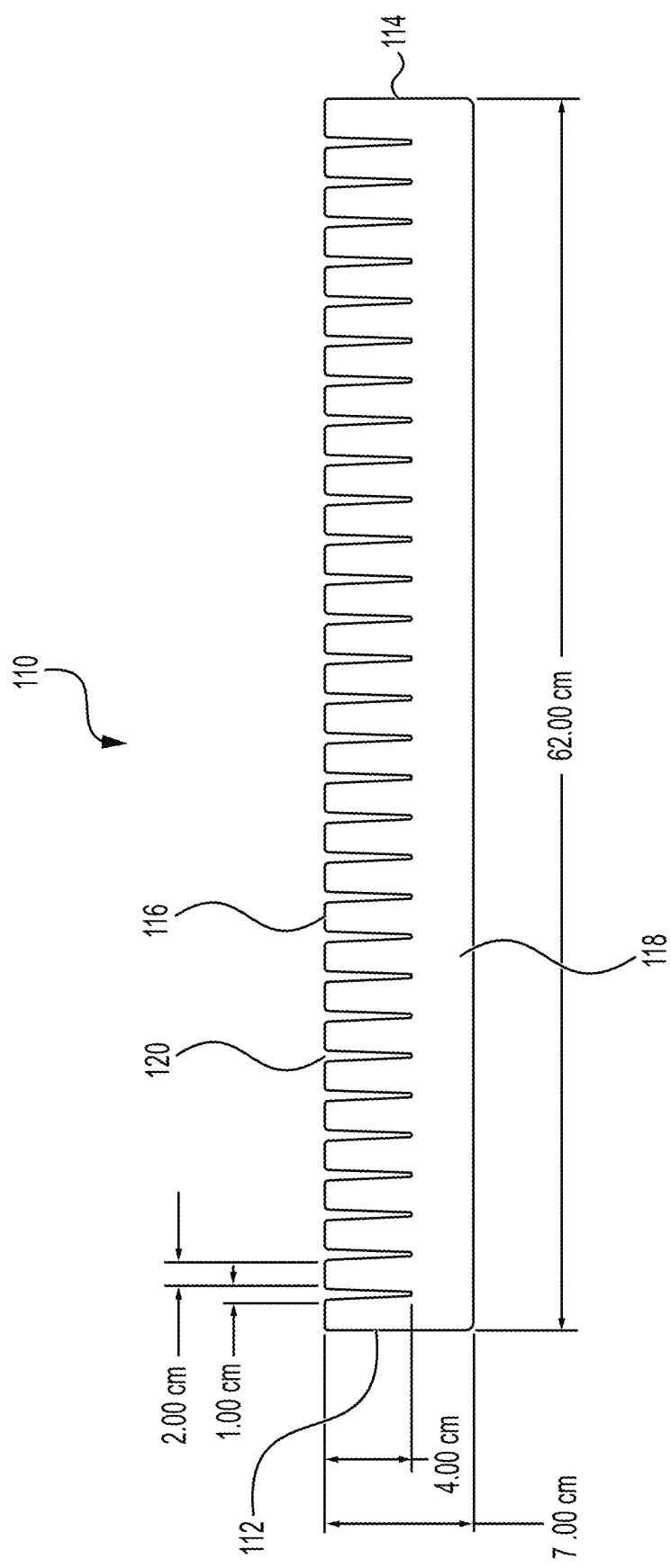
FIG. 2A is a side view of a disposable gauze counter according to the present subject matter.
Figure 2B:
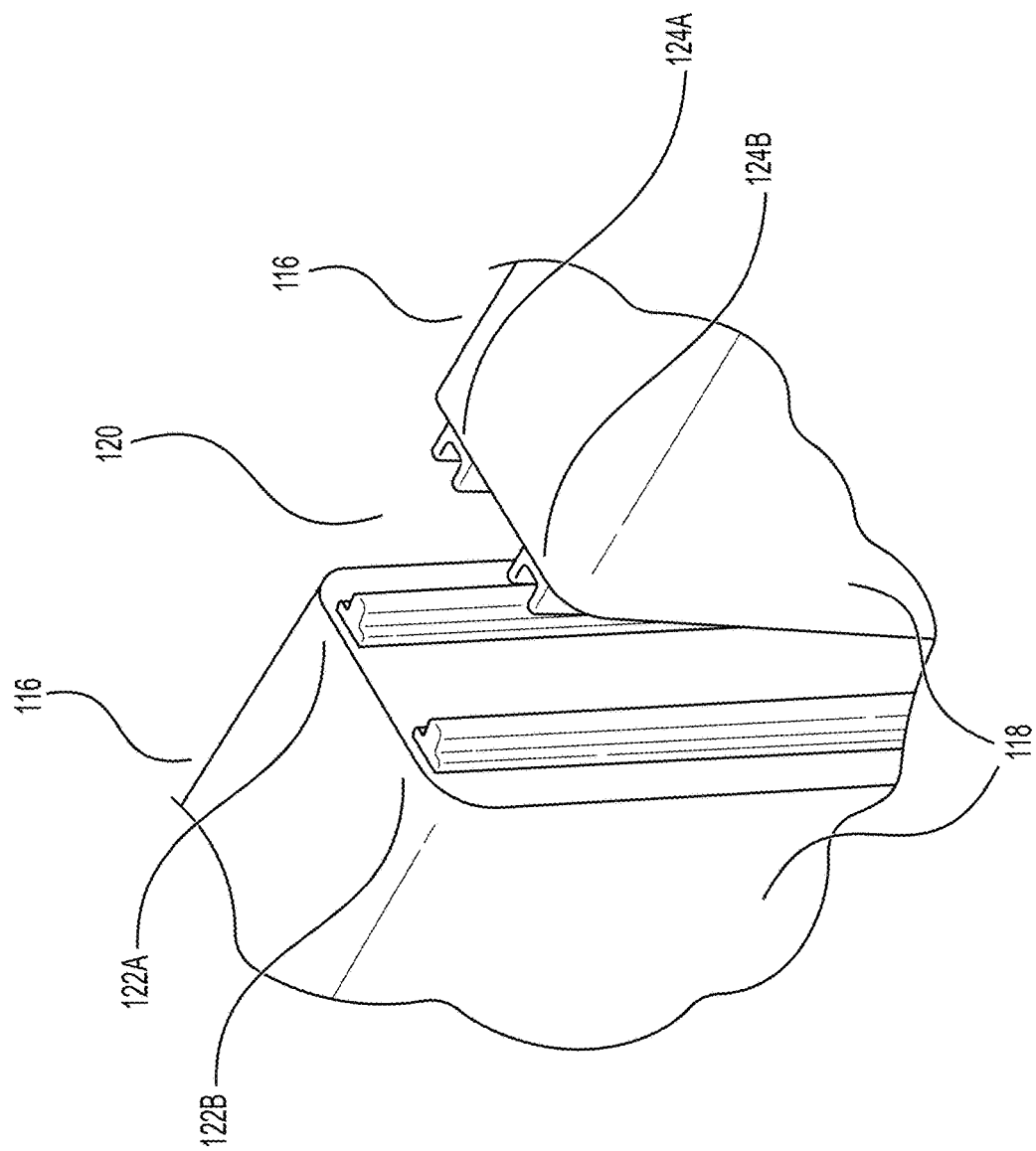
FIG. 2B is a perspective view of a disposable gauze counter illustrating an alternative one of the plurality of resealable airtight clips.

As illustrated in FIGS. 2A and 2B, the disposable gauze counter 110 includes a plurality of resealable airtight clips 120. Each disposable gauze counter 110 has opposing first 112 and second ends 114 and opposing top 116 and bottom sides 118, with each of the plurality of resealable airtight clips 120 disposed between the first end 112 and the second end 114 and generally extending from the top side 116 of the disposable gauze counter 110 towards the bottom side 118 of the disposable gauze counter 110. Each of the plurality of resealable airtight clips 120 can, but do not necessarily, extend all the way to the bottom side 118 of the disposable gauze counter 110. That is, each of the plurality of resealable airtight clips 120 can extend from the top side 116 of the disposable gauze counter 110 along part of the distance between the top side 116 and the bottom side 118 of the disposable gauze counter 110. In an embodiment, each of the resealable airtight clips 120 have a same length. In another embodiment, each of the resealable airtight clips 120 have a different length.

The plurality of resealable airtight clips 120 each comprise an opening having opposed first and second sides, the first side and the second side of each opening each having a pair of engaging members 122a, 122b, 124a, 124b disposed thereon, wherein when the first side engaging members 122a, 122b, and the second side engaging members 124a, 124b of a same opening are respectively pressed together each pair of the engaging members 122a, 124a, and 124a, 124b form interlocking seals.

Figure 3:
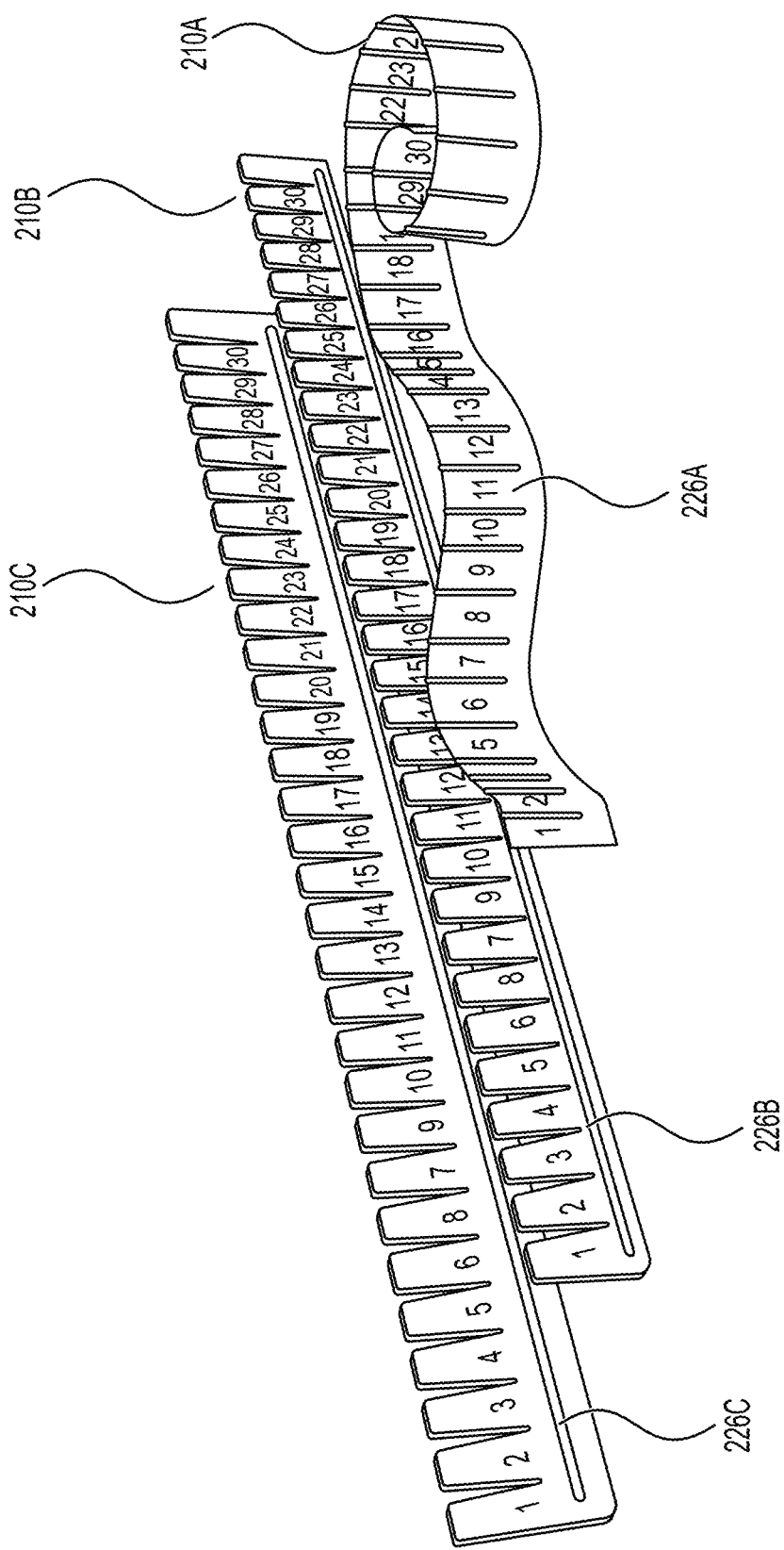
FIG. 3 is a perspective view of a plurality of disposable gauze counters according to the present subject matter.

In an alternative embodiment illustrated in FIG. 3, a plurality of disposable gauze counters 210a, 210b, 210c are provided, and each disposable gauze counter 210a, 210b, 210c includes a plurality of resealable airtight clips as described herein, thereby providing an overall disposable gauze system. Each of the plurality of disposable gauze counters 210a, 210b, 210c has a label 226a, 226b, 226c extending from the first end to the second end along the bottom side and below the plurality of resealable airtight clips, wherein the label 226a, 226b, 226c identifies the particular disposable gauze counter as being specifically used to retain surgical gauze, surgical towels, radio-opaque gauze, or the like.

The disposable gauze counter as disclosed herein may be used for retention and visible indication of surgical gauzes used during a surgical procedure and retrieved from the patient. The surgical gauzes retained by the disposable gauze counter may include surgical gauzes, surgical towels, radiopaque surgical gauzes, or any other absorbent material now known or developed in the future for use as a disposable absorbent material used during a surgical procedure and intended to be removed before the procedure is concluded. A plurality of disposable gauze counters bearing different labels may be used to separately track the number of each kind of surgical gauze used during a particular procedure.

In an embodiment, the disposable gauze counter may include numbering or other labelling of each of the plurality of resealable airtight clips to facilitate easy visual confirmation of the number of surgical gauzes retained therein during a procedure. In an embodiment, each disposable gauze counter may have at least 30 resealable airtight clips.

In an embodiment, a disposable gauze counter intended for retaining standard surgical gauzes may have a total length of about 62 cm, a total width of about 4 cm, and a total thickness of about 0.1 cm.

In an embodiment, a disposable gauze counter intended for retaining large sponges may have a total length of about 62 cm, a total width of about 7 cm, and a total thickness of about 1 cm.

In an embodiment, the disposable gauze counter may be made of any suitable material. In some, non-limiting embodiments, the disposable gauze counter may be made of polyethylene and the plurality of resealable airtight clips may be made of polypropylene. The disposable gauze counter may be stiff or flexible, as seen in FIG. 3.

In use, the disposable gauze counter assists surgeons in keeping an accurate count of the surgical gauzes, sponges, and the like used during a surgical procedure to ensure that all such absorbent materials are removed from a patient before conclusion of the procedure. The disposable gauze counter may be particularly effective as the gauzes retained therein are visible to all working in the surgical suite and in some embodiments are counted separately by type of absorbent material to further assist in keeping accurate counts.

It is to be understood that the disposable gauze counter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A disposable gauze counter comprising:
a plurality of resealable airtight clips disposed between a first end and a second end of the disposable gauze counter, wherein each of the plurality of resealable airtight clips extend from a top side of the disposable gauze counter towards a bottom side of the disposable gauze counter; the plurality of resealable airtight clips each comprising:
an opening having opposed first and second sides; and
the first side and the second side of each said opening each having at least one engaging member disposed thereon;
wherein when each of the at least one first side engaging members and each of the at least one second side engaging members located at a same opening are pressed together, each said first side and second side engaging members form an interlocking seal.

2. The disposable gauze counter as recited in claim 1, comprising a label adjacent to each of the plurality of resealable airtight clips.

3. The disposable gauze counter as recited in claim 1, wherein the first side and the second side of each of the plurality of resealable airtight clips each have two engaging members disposed thereon.

4. The disposable gauze counter as recited in claim 1, wherein each of the plurality of resealable airtight clips are adapted for holding a surgical gauze.

5. The disposable gauze counter as recited in claim 1, wherein each of the plurality of resealable airtight clips are adapted for holding a surgical sponge.

6. The disposable gauze counter as recited in claim 1, wherein each of the plurality of resealable airtight clips are adapted for holding a radiopaque surgical gauze.

7. A disposable gauze system comprising a plurality of disposable gauze counters of claim 1.

8. The disposable gauze system of claim 7, wherein each of the plurality of disposable gauze counters comprises a label extending from the first end of the disposable gauze counter to the second end of the disposable gauze counter and below the plurality of resealable airtight clips.

9. The disposable gauze system of claim 7, wherein each of the plurality of disposable gauze counters is adapted for holding a different absorbent material.

* * * * *